United States Patent [19]

Sanderson et al.

[11] Patent Number: 4,978,785
[45] Date of Patent: Dec. 18, 1990

[54] OXIDATION OF POLYOXYPROPYLENE GLYCOLS TO ACIDS AND KETONES

[75] Inventors: John R. Sanderson, Leander; John M. Larkin, Austin, both of Tex.

[73] Assignee: Texaco Chemical Company, White Plains, N.Y.

[21] Appl. No.: 448,428

[22] Filed: Dec. 11, 1989

[51] Int. Cl.$^5$ .................. C07C 45/29; C07C 49/175; C07C 51/245; C07C 53/126
[52] U.S. Cl. .................................... 562/537; 568/405
[58] Field of Search ...................... 568/405; 562/537

[56] References Cited

U.S. PATENT DOCUMENTS

| | | | |
|---|---|---|---|
| 2,312,468 | 3/1943 | Ebel et al. | 562/537 |
| 2,653,972 | 9/1953 | Ash et al. | 562/537 |
| 2,659,754 | 11/1953 | Ash et al. | 562/537 |
| 2,886,590 | 5/1954 | Montgomery et al. | 562/537 |

FOREIGN PATENT DOCUMENTS 88962 9/1983 European Pat. Off. ............ 562/537

Primary Examiner—J. E. Evans
Attorney, Agent, or Firm—Jack H. Park; Kenneth R. Priem; Carl G. Ries

[57] ABSTRACT

Carboxylic acid derivatives and methyl ketone derivatives of polyoxypropylene glycols are prepared by the selective nitric acid oxidation of a polyoxypropylene glycol in the presence of an alkali metal nitrite. If the alkali metal nitrite is added to an aqueous solution of nitric acid and the polyoxypropylene glycol is thereafter added, carboxylic acid derivatives of the polyoxypropylene glycol are provided. If a mixture of an alkali metal nitrite and a polyoxypropylene glycol is added to an aqueous solution of nitric acid, a reaction product containing a predominant amount of methyl ketone derivatives of the polyoxypropylene glycol is provided.

8 Claims, No Drawings

4,978,785

OXIDATION OF POLYOXYPROPYLENE GLYCOLS TO ACIDS AND KETONES

BACKGROUND OF THE INVENTION

1. Technical Field of The Invention

This invention relates to a method for the oxidation of polyoxypropylene glycols. More particularly, this invention relates to the method for preparing carboxylic acid derivatives and methyl ketone derivatives of polyoxypropylene glycols. Still more particularly, this invention relates to a method for the controlled selective nitric acid oxidation of a polyoxypropylene glycol in order to selectively provide carboxylic acid derivatives or methyl ketone derivatives thereof.

It has been discovered in accordance with the present invention that when the nitric acid oxidation of a polyoxypropylene glycol is conducted in the presence of an alkali metal nitrite the oxidation can be conducted under acid conditions in order to selectively provide carboxylic acid derivatives or methyl ketone derivatives of the polyoxypropylene glycol.

In accordance with one embodiment of the present invention, the alkali metal nitrite is added to an aqueous solution of nitric acid and the polyoxypropylene glycol is thereafter added in order to provide carboxylic acid derivatives of the polyoxypropylene glycol.

In accordance with another embodiment of the present invention, a mixture of an alkali metal nitrite and a polyoxypropylene glycol is added to an aqueous solution of nitric acid in order to provide a reaction product containing a predominant amount of methyl ketone derivatives of the polyoxypropylene glycol.

2. Prior Art

General information on oxidation with nitric acid and nitrogen oxides is given in Chapter IV by Yoshiro Ogata (pp. 295–317) of the text "Oxidation in Organic Chemistry, Part C," edited by Walter S. Trahanovsky, New York Academic Press, 1978.

Languar et al. U.S. Pat. No. 4,793,905 discloses a method using a transition metal electrocatalyst for the manufacture, for example, of an ester or a carboxylic acid such as ethyl acetate from an alcohol such as ethanol.

The oxidation of polyoxyethylene glycols to the corresponding polyoxyethylene dicarboxylic acids using molecular oxygen and a supported platinum catalyst is disclosed in Morris et al. U.S. Pat. No. 4,256,916.

In U.S. Pat. No. 4,233,460, Willis et al. disclose an extremely mild oxidative process for converting alkoxy alkanols to the corresponding acids with an alkali metal hydroxide and tert.-butyl hydroperoxide in the presence of a catalytic amount of palladium.

U. K. patent application GB 2 152 050 A discloses a process for preparing alkali metal salts of monoalkyl ethers of polyoxyethylene monoalkyl ethers of polyoxyethylene glycols by oxidizing the monoalkyl ether in solution an aqueous alkaline medium with oxygen in the presence of a platinum or palladium catalyst.

SUMMARY OF THE PRESENT INVENTION

The present invention is directed to a method for the controlled nitric acid oxidation of a polyoxypropylene glycol in order to provide a reaction product containing a predominant amount of a predetermined oxidation product, the process being conducted by:

a. Preparing a first feedstock comprising an aqueous solution of nitric acid containing from about 5 to about 50 wt.% of nitric acid, b. Preparing a feedstock comprising a polyoxypropylene glycol;

c. Adding from about 0.1 to about 1 parts by weight of an alkali metal nitrite per 100 parts by weight of nitric acid to one of said feedstocks;

d. Charging one of said feedstocks to a reaction vessel;

e. Establishing reaction conditions in the reaction vessel at atmospheric pressure, including a temperature of about 20° to about 100° C.;

f. Continuously adding the other feedstock to the reaction vessel over a period of about 5 to 20 hours with agitation while maintaining the desired reaction conditions in order to provide a reaction mixture comprising a polyoxypropylene glycol oxidation product;

g. Withdrawing the reaction mixture from the reaction vessel; and h. Recovering a polyoxypropylene glycol oxidation product from the reaction mixture;

i. The polyoxypropylene glycol feedstock having the

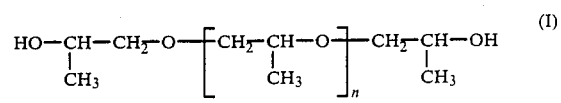

j. The polyoxypropylene oxidation reaction product being a carboxylic reaction product or a methyl ketone reaction product selected from the group consisting of reaction products having the formulae:

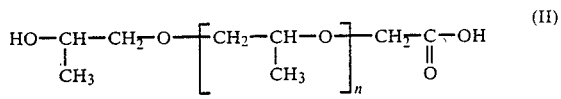

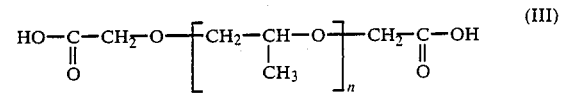

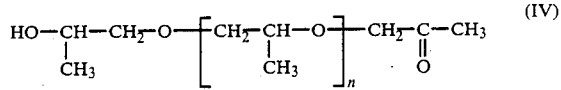

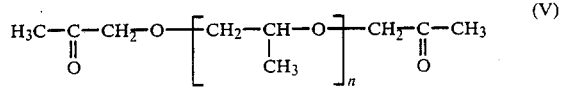

wherein n is a positive number having an average value of about 2 to about 170.

DETAILED DESCRIPTION

The starting materials for the process of the present invention are a polyoxypropylene glycol having an average molecular weight of about 200 to about 10,000, an aqueous solution of nitric acid and an alkali metal nitrite.

The polyoxypropylene glycol to be used as a feedstock in accordance with the present invention is suitably a polyoxypropylene glycol having the formula:

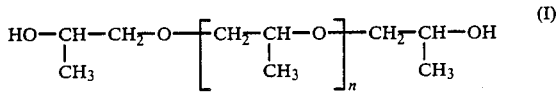

(I)

wherein n is a positive number having an average value of about 2 to about 170.

Examples of polyoxypropylene glycols that may be used as feedstocks in accordance with the present invention, either alone or in admixture include, for example, products such as a polyoxypropylene glycol having an average molecular weight of about 230 (wherein n in formula I has an average value of about 2), a polyoxypropylene glycol having an average molecular weight of about 400 (wherein in formula I the value of n is between about 5 and about 6), a polyoxypropylene glycol having an average molecular weight of about 2,000 (wherein in formula I the value of n is about 33), etc., and a polyoxypropylene glycol having an average molecular weight of about 4,000 (wherein n in formula I has the value of about 60).

The oxidizing agent to be used in accordance with the present invention is nitric acid. Although it is technically feasible to use concentrated nitric acid in conducting the process of the present invention, for reasons for safety and process control, it is preferable to use an aqueous solution of nitric acid which contains from about 5 to about 50 wt.% of nitric acid, and more preferably, an aqueous solution of nitric acid containing from about 20 to about 40 wt.% of nitric acid.

The alkali metal nitrite to be used in accordance with the present invention may be any appropriate alkali metal nitrite such as sodium nitrite, potassium nitrite, etc. Preferably the alkali metal nitrite is sodium nitrite and it should be used in an amount within the range of about 0.1 to about 1 parts by weight per 100 parts of nitric acid or glycol.

REACTION CONDITIONS

The oxidation reaction of the present invention is preferably conducted at about atmospheric pressure for reasons of safety and process control.

The reaction is preferably conducted at a temperature of about 20° to about 100° C. and, still more preferably, at a temperature of about 50° to about 100° C.

In order to maintain good process control and for reasons of safety, it is preferable to add the aqueous solution of nitric acid to a reaction vessel and to establish the appropriate reaction temperature and then to slowly add the polyoxypropylene reactant over a period of time within the range of about 5 to about 20 hours, such as about 5 to 15 hours, with agitation.

However, it is feasible and, if desired, the polyoxypropylene glycol can be initially charged to the reaction vessel and the nitric acid can be the reactant that is slowly added over the course of the reaction.

If the reaction product that is desired is a carboxylic acid derivative of the polyoxypropylene glycol, the alkali metal nitrite should be added to the aqueous solution of nitric acid.

If the desired oxidation reaction product is a methyl ketone derivative of the polyoxypropylene glycol, the sodium nitrite should be added to the reaction vessel together with the polyoxypropylene glycol.

At the completion of the reaction, the reaction mixture may be cooled and water and excess nitric acid may be removed by any suitable means, such as by evaporation, to thereby provide a reaction mixture comprising the polyoxypropylene glycol oxidation product.

The desired polyoxypropylene oxidation product can be recovered from the reaction mixture by any suitable means such as distillation, etc.

The invention will be further illustrated by the following specific examples which are given by way of illustration and not as limitations on the scope of the invention.

EXAMPLES

Procedure

In the normal procedure for running an experiment, a desired amount of nitric acid and water were charged to a reaction vessel equipped with a water cooled condenser, temperature sensing means and agitator and means for the continuous addition of the other reactant.

When the desired reaction product was a carboxylic acid derivative of the polyoxypropylene glycol, sodium nitrite was added to the reaction vessel together with the nitric acid in the desired amount.

Thereafter, the reaction mixture was heated to the desired temperature and the polyoxypropylene glycol was added with agitation over the desired reaction time such as a reaction time of 15 hours. At the end of that time, the reaction mixture was cooled and water and excess nitric acid were removed by evaporation, for example at a temperature of about 80° to 85° C. and a pressure of about 100 mm Hg.

When the desired reaction product was a methyl ketone derivative of the polyoxypropylene glycol, the sodium nitrite was dissolved in the polyoxypropylene glycol and this was added to the reaction vessel over a period of time.

The experiments performed and the results obtained are set forth in the following table.

TABLE I

| | PREPARATION OF PPG-DICARBOXYLATES BY NITRIC ACID OXIDATION | | | | | | | | | | |
|---|---|---|---|---|---|---|---|---|---|---|---|
| Notebook Number | % PPG-230 | % NHO3 | g | g H2O | Initiator | g | Time (Hr) | Temp. (°C.) | Product Wt. (g) | IR % C=O | % Acid[b] | N (%) |
| 6465-17 | 25 | 70 | 50 | 75 | NaNO2 | 0.10 | 15 | 50 | 19.6 | >50% —COOH | — | — |
| 6465-21 | 23 | 70 | 50 | 50 | NaNO2 | 0.10 | 6 | 80 | 19.1 | — | 37.5 | 0.51 |
| 6465-26 | 50 | 70 | 100 | 100 | NaNO2 | 0.20 | 6 | 80 | 41.3 | 31 | 35.2 | — |
| 6465-27 | 50 | 70 | 100 | 100 | NaNO2 | 0.20 | 6 | 60 | 45.0 | >50% —COOH | 56.5 | — |
| 6465-28 | 50 | 70 | 100 | 100 | NaNO2 | 0.20 | 6 | 100 | 43.5 | 30 | 41.9 | — |
| 6465-29* | 50 | 70 | 50 | 50 | NaNO2 | 0.25 | 15 | 50 | 44.2 | 35 | 0.3 | 0.41 |
| 6465-31* | 50 | 70 | 70 | 60 | NaNO2 | 0.50 | 15 | 50-70 | 38.5 | 42 | 0.6 | 0.48 |
| 6465-32* | 50 | 70 | 70 | 100 | NaNO2 | 0.50 | 15 | 50-70 | 38.7 | 48 | 0.5 | 0.52 |
| 6465-33 | 50 | 70 | 100 | 100 | NaNO2 | 0.10 | 15 | 55 | 43.0 | O‖SOiSO—C:COOH | 51.4 | 0.72 |

TABLE I-continued

PREPARATION OF PPG-DICARBOXYLATES BY NITRIC ACID OXIDATION

| Notebook Number | PPG-230 | % NHO3 | g | g H2O | Initiator | g | Time (Hr) | Temp. (°C.) | Product Wt. (g) | IR % C=O | % Acid[b] | N (%) |
|---|---|---|---|---|---|---|---|---|---|---|---|---|
| 6465-34 | 50 | 70 | 150 | 100 | NaNO2 | 0.10 | 15 | 55 | 43.5 | —COOH only | 97.7 | 0.66 |
| 6465-35 | 50 | 70 | 160 | 100 | NaNO2 | 0.10 | 15 | 55 | 40.3 | —COOH only | 95.6 | — |
| 6465-36[a] | 50 | 70 | 160 | 100 | NaNO2 | 0.10 | 15 | 60-80 | 40.7 | —COOH only | 78.6 | — |
| 6465-37[a] | 50 | 70 | 150 | 100 | NaNO2 | 0.10 | 15 | 60 | 37.1 | —COOH only | 88.7 | — |

*NaNO2 was dissolved in the polyol and this was added to the dilute nitric acid.
[a]Inverse addition, i.e. acid added to the polyol.
[b]Based on titration with KOH.

Having thus described our invention, what is claimed is:

1. A method for the controlled nitric acid oxidation of a polyoxypropylene glycol in order to provide a reaction product containing a predominant amount of a predetermined oxidation product which comprises the steps of:
   (a) preparing a first feedstock comprising an aqueous solution of nitric acid containing from about 5 to about 50 wt.% of nitric acid,
   (b) preparing a second feedstock comprising a polyoxypropylene glycol,
   (c) adding from about 0.1 to about 1 parts by weight of an alkali metal nitrite per 100 parts by weight of said nitric acid to one of said feedstocks,
   (d) charging one of said feedstocks to a reaction vessel,
   (e) establishing reaction conditions in said reaction vessel at about atmospheric pressure including a temperature of about 20° to about 100° C.,
   (f) continuously adding the other of said feedstocks to said reaction vessel over a period of about 5 to about 20 hours with agitation while maintaining said reaction conditions to provide a reaction mixture comprising a polyoxypropylene glycol oxidation reaction product,
   (g) withdrawing said reaction mixture from said reaction vessel, and
   (h) recovering said polyoxypropylene glycol oxidation product from said reaction mixture,
   (i) said polyoxypropylene glycol feedstock having the formula:

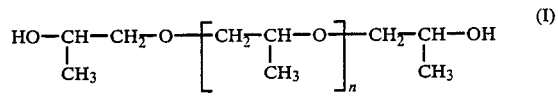
(I)

(j) said polyoxypropylene oxidation reaction product being a carboxylic acid reaction product or a methyl ketone reaction product selected from the group consisting of reaction products having the formulae:

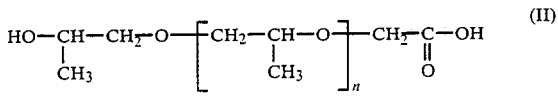
(II)

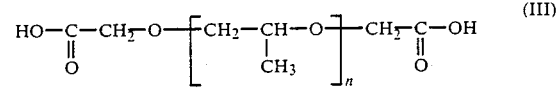
(III)

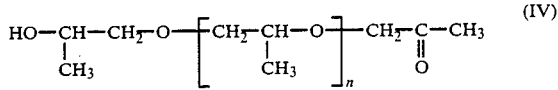
(IV)

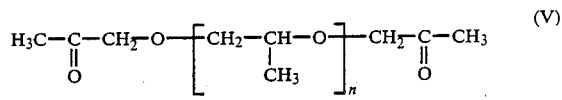
(V)

wherein n is a positive number having an average value of about 2 to about 170.

2. A method as in claim 1 wherein the alkali metal nitrite is sodium nitrite and wherein, in the formulae, "n" has a value of about 2.

3. A method as in claim 2 wherein the sodium nitrite is added to said first nitric acid feedstock and wherein the polyxoypropylene glycol oxidation product contains at least about 25 mole percent, based on the polyoxypropylene glycol charge, of polyoxypropylene mono- and dicarboxylic acids having formulas II and III.

4. A method as in claim 2 wherein the sodium nitrite is added to said second polyoxypropylene glycol feedstock and wherein the polyxoypropylene glycol oxidation product contains at least about 10 mole percent, based on the polyoxypropylene glycol charge, of polyoxypropylene mono- and di-ketones having formulas IV and V.

5. A method for the controlled nitric acid oxidation of a polyoxypropylene glycol in order to provide a reaction product containing a predominant amount of carboxylic acid derivatives of said polyoxypropylene glycol which comprises the steps of:
   (a) preparing a first feedstock consisting essentially of an aqueous solution of nitric acid containing from about 5 to about 50 wt.% of nitric acid and from about 0.1 to about 1 parts by weight of an alkali metal nitrite per 100 parts by weight of said nitric acid,
   (b) charging said feedstock to a reaction vessel,
   (c) establishing reaction conditions in said reaction vessel at about atmospheric pressure including a temperature of about 50° to about 100° C.,
   (d) continuously adding a second feedstock consisting essentially of a polyoxypropylene glycol to said reaction vessel over a period of about 5 to about 15 hours with agitation while maintaining said reaction conditions to provide a reaction mixture comprising carboxylic acid derivatives of said polyoxypropylene glycol,
   (e) withdrawing said reaction mixture from said reaction vessel, and
   (f) recovering said carboxylic acid derivatives of said polyoxypropylene glycol from said reaction mixture,
   (g) said polyoxypropylene glycol feedstock having the formula:

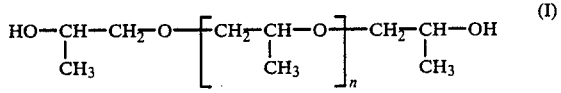

(h) said carboxylic acid derivatives of said polyoxypropylene glycol having the formulae:

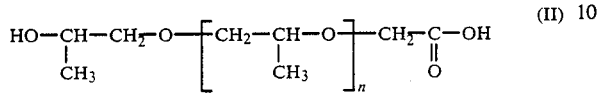

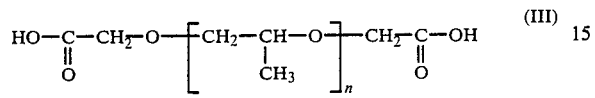

wherein n is a positive number having an average value of about 2 to about 170.

6. A method as in claim 5 wherein the alkali metal nitrite is sodium nitrite and "n" has a value of about 2.

7. A method for the controlled nitric acid oxidation of a polyoxypropylene glycol in order to provide a reaction product containing a significant amount of methyl ketone derivatives of said polyoxypropylene glycol which comprises the steps of:
(a) preparing a first feedstock consisting essentially of an aqueous solution of nitric acid,
(b) charging said feedstock to a reaction vessel,
(c) establishing reaction conditions in said reaction vessel at about atmosphereic pressure including a temperature of about 50° to about 100° C.,
(d) continuously adding a second feedstock to said reaction vessel over a period of about 5 to about 15 hours with agitation while maintaining said reaction conditions, said second feedstock consisting essentially of a polyoxypropylene glycol and from about 0.1 to about 1 parts by weight of an alkali metal nitrite per 100 parts by weight of said nitric acid, to thereby provide a reaction mixture comprising said methyl ketone derivatives of said polyoxypropylene glycol,
(e) withdrawing said reaction mixture from said reaction vessel, and
(f) recovering said methyl ketone derivatives of said polyoxypropylene glycol from said reaction mixture,
(g) said polyoxypropylene glycol feedstock having the formula:

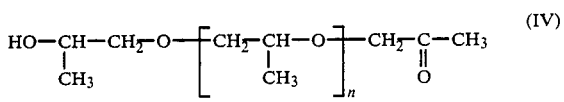

(h) said methyl ketone derivatives of said polyoxypropylene glycol having the formulae:

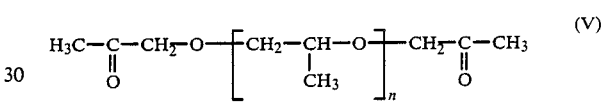

wherein n is a positive number having an average value of about 2 to about 170.

8. A method as in claim 7 wherein the alkali metal nitrite is sodium nitrite and "n" has a value of about 2.

* * * * *